United States Patent
Senoo et al.

(10) Patent No.: US 12,227,735 B2
(45) Date of Patent: Feb. 18, 2025

(54) PRODUCING METHOD OF STRESS RELIEVER

(71) Applicant: FUJIWARA TECHNO-ART CO., LTD., Okayama (JP)

(72) Inventors: Satoko Senoo, Okayama (JP); Natsuki Fukano, Okayama (JP); Takashi Bungo, Hiroshima (JP)

(73) Assignee: FUJIWARA TECHNO-ART CO., LTD., Okayama (JP)

(*) Notice: Subject to any disclaimer, the term of this patent is extended or adjusted under 35 U.S.C. 154(b) by 0 days.

(21) Appl. No.: 18/364,080

(22) Filed: Aug. 2, 2023

(65) Prior Publication Data

US 2023/0374442 A1 Nov. 23, 2023

Related U.S. Application Data

(63) Continuation of application No. 17/169,901, filed on Feb. 8, 2021, now abandoned.

(30) Foreign Application Priority Data

Jan. 20, 2021 (JP) ................................ 2021-007382

(51) Int. Cl.
  *C12N 1/14* (2006.01)
  *A23K 10/30* (2016.01)
  *A23K 50/75* (2016.01)
  *A61K 36/062* (2006.01)

(52) U.S. Cl.
  CPC ............... *C12N 1/14* (2013.01); *A23K 10/30* (2016.05); *A23K 50/75* (2016.05); *A61K 36/062* (2013.01)

(58) Field of Classification Search
  CPC ............ C12N 1/14; A23K 50/75; A23K 10/30
  See application file for complete search history.

(56) References Cited

FOREIGN PATENT DOCUMENTS

| CN | 106177705 A | | 12/2016 | |
|---|---|---|---|---|
| CN | 107760612 A | * | 3/2018 | ........... A23K 20/189 |
| JP | H1175709 A | | 3/1999 | |
| JP | 2003235465 A | | 8/2003 | |
| JP | 2007-325580 A | | 12/2007 | |
| WO | 2014/082847 A1 | | 6/2014 | |

OTHER PUBLICATIONS

Kyotaro Ichikawa, et al., "Efficient production of recombinant tannase in Aspergillus oryzae using an improved glucoamylase gene promotor", Journal of Bioscience and Bioengineering, Feb. 2020, pp. 150-154, vol. 129, Issue No. 2, doi: 10.1016/j.jbiosc.2019.08.002. Epub Sep. 3, 2019. PMID: 31492608. (Year: 2019).

J. Abdulla, et al., "Exogenous tannase improves feeding value of a diet containing field beans (*Vicia faba*) when fed to broilers", 2016. British Poultry Science, 57 (2), pp. 246-250. (Year: 2016).

David Mitchell, et al., Solid-State Fermentation Bioreactors: Fundamentals of Design and Operation, Springer-Verlag Berlin Heidelberg, 2006, pp. 17-23, 26, 36-42 (Year: 2006).

* cited by examiner

*Primary Examiner* — Ruth A Davis
(74) *Attorney, Agent, or Firm* — McDonald Hopkins LLC

(57) ABSTRACT

Provided is a method of producing a stress reliever that reduces a decrease in productivity of livestock at the time of stress load by feeding the stress reliever to the livestock. The method of producing the stress reliever includes solid-culturing a substrate with the filamentous fungi, in which the stress reliever reduces a decrease in productivity of livestock at the time of stress load.

8 Claims, 6 Drawing Sheets

PRODUCING METHOD OF STRESS RELIEVER

FIELD

The present invention relates to a method of producing a stress reliever.

BACKGROUND

Patent Literature 1 cited below has described a method for selecting specific *Aspergillus Oryzae* (IK-05074 strain) that excellently breeds in a culture medium to which sodium deoxycholate is added and inoculating the selected *Aspergillus Oryzae* (IK-05074 strain) to brown rice to produce a solid-cultured product. In this solid-cultured product, activity of acid-resistant α-amylase, acidic protease, and acidic carboxypeptidase is higher than that of a cultured product obtained by culturing *Aspergillus Kawachii* and this solid-cultured product is said to have the effect of an increase in the body weight of chicks.

CITATION LIST

Patent Literature

Patent Literature 1: Japanese Patent Application Laid-open No. 2007-325580

SUMMARY

Technical Problem

Patent Literature 1 has not described that a decrease in productivity of livestock is reduced by relieving stress using the solid-cultured product of filamentous fungi when the stress is applied to the livestock.

When the stress is applied to livestock, the productivity of the livestock is reduced due to reduction in the ingestion amount of feedstuff or a decrease in the body weight of the livestock.

An object of the present disclosure is to provide a method of producing a stress reliever that reduces the decrease in productivity of livestock at the time of stress load by orally feeding the stress reliever to the livestock.

Solution to Problem

The above-described problem is solved by a method of producing a stress reliever, the method including: solid-culturing a substrate with filamentous fungi to obtain a solid-cultured product, wherein the stress reliever reduces a decrease in productivity of livestock at the time of stress load.

The stress reliever produced by the method of producing the stress reliever preferably reduces one or more decreases in productivity of livestock at the time of stress load by relieving the stress of the livestock ingesting the stress reliever, the one or more decreases being among body weight reduction, a decrease in the ingestion amount of feedstuff, a decrease in an egg weight, a decrease in an eggshell thickness, and a decrease in a yolk weight.

In the method of producing the stress reliever, the filamentous fungi are preferably fungi not producing mold poison. In the method of producing the stress reliever, the fungi not producing mold poison are preferably *Aspergillus oryzae, Aspergillus sojae, Aspergillus luchuensis, Aspergillus niger*, or *Aspergillus awamori* not producing mold poison.

In the method of producing the stress reliever, the solid-cultured product preferably includes polysaccharides constituting hyphae of the filamentous fungi. In the method of producing the stress reliever, the solid-cultured product preferably includes an enzyme having activity. In the method of producing the stress reliever, the solid-cultured product preferably includes viable fungi of the filamentous fungi.

In the method of producing the stress reliever, the method may further include determining the solid-cultured product alone obtained by solid-culturing the substrate with the filamentous fungi to be the stress reliever or blending the solid-cultured product obtained by solid-culturing the substrate with the filamentous fungi with a feeding substance.

Advantageous Effects of Invention

According to the present disclosure, a method of producing a stress reliever that reduces a decrease in productivity of livestock at the time of stress load by orally feeding the stress reliever to the livestock can be provided.

DESCRIPTION OF EMBODIMENTS

Figure 1:
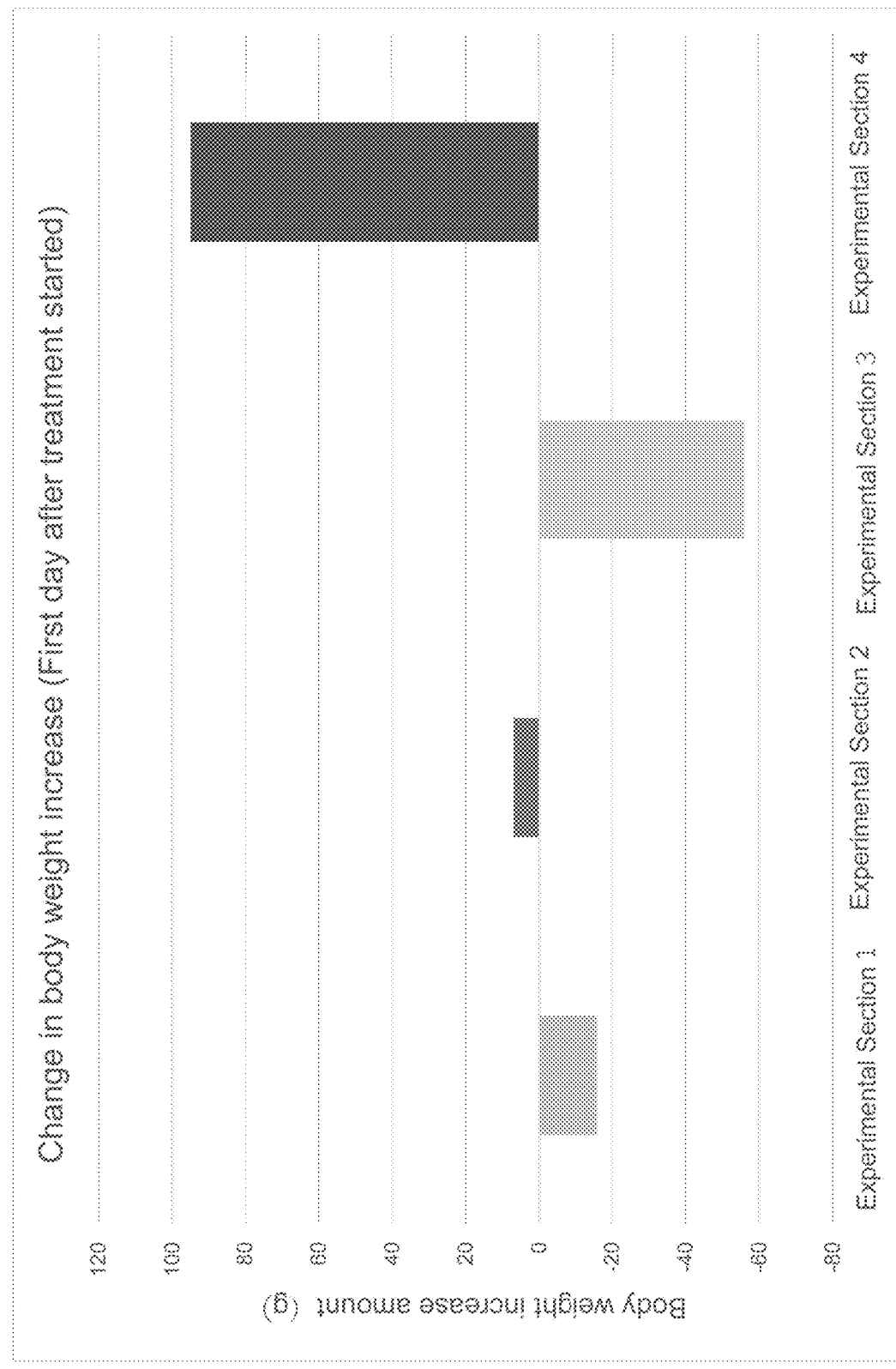
FIG. 1 is a graph illustrating the amount of body weight change (g) on the next day (the first day) after hot environment treatment started.

Hereinafter, the embodiment of the method of producing the stress reliever and the stress reliever produced by the method will be described.

The stress reliever is used by orally feeding the stress reliever to livestock and includes the solid-cultured product of filamentous fungi. The effect of reducing the decrease in productivity of livestock can be obtained by orally feeding the stress reliever to livestock. The stress reliever can be produced by the method of producing the stress reliever including solid-culturing a substrate with filamentous fungi to obtain the solid-cultured product.

As the filamentous fungi used in the above production method, the fungi not producing mold poison are preferably used. Ingestion of the fungi not producing mold poison to livestock is safe. Examples of the filamentous fungi not producing mold poison include *Aspergillus oryzae, Aspergillus sojae, Aspergillus luchuensis, Aspergillus niger*, or *Aspergillus awamori* not producing mold poison. As these filamentous fungi, seed fungi for the fermentation of fermented foods are commercially available or the filamentous fungi can be obtained at NITE Biological Resource Center (NBRC). The filamentous fungi may be a wild strain of which gene is not modified or may be filamentous fungi of which gene is modified by a gene technological method as described below.

Examples of the mold poison include aflatoxin, deoxynivalenol, ochratoxin, fumonisin, zearalenone, patulin, sterigmatocystin, or fusarium toxin.

The solid-cultured product of the filamentous fungi preferably includes polysaccharides constituting hyphae of the filamentous fungi. When the cultured product including the polysaccharides and the filamentous fungi are fed together to livestock, the decrease in productivity of livestock caused by stress can be more remarkably reduced. Although the detailed mechanism is unclear, it is presumed that the immunity of the livestock ingesting the polysaccharides is improved, whereby the decrease in productivity of livestock caused by stress is reduced.

The solid-cultured product of the filamentous fungi preferably includes an enzyme having activity. When the enzyme having the activity is, for example, an enzyme that improves the digestion ratio of the feedstuff, nutrient contents are easily taken into the body of the livestock by degrading the feedstuff fed by livestock with the enzyme inside the body of livestock and thus feedstuff efficiency can be improved. This degradation action is performed inside the body of livestock and thus digestion of the feedstuff by the livestock can be promoted. Although the detailed mechanism is unclear, it is presumed that the decrease in productivity of the livestock caused by stress is reduced by easily taking the various nutrient contents into the body of the livestock. In the outside of the body of livestock, the degradation action can also be obtained in the case where the feedstuff and the solid-cultured product of the filamentous fungi are mixed and culture or enzyme reaction is performed.

The solid-cultured product of the filamentous fungi preferably includes viable fungi of the filamentous fungi. For example, when the solid-cultured product includes the viable fungi, the production of the stress reliever can be easily increased by, for example, adding the substrate described below to the cultured product to perform secondary culture. According to this method, the stress reliever can be remarkably easily obtained because the seed fungi are not required to be subdivided and obtained or the seed fungi are not required to be purchased.

In order to form the solid-cultured product having the enzyme activity, the solid-cultured product of the filamentous fungi may be determined to be the stress reliever without applying excessive heating to the solid-cultured product. The excessive heating refers to heating to the extent that the enzyme activity is lost. In order that the solid-cultured product includes the viable fungi of the filamentous fungi, the solid-cultured product of the filamentous fungi may be used as the stress reliever without performing excessive heating to the extent that the filamentous fungi become extinct.

For example, in the case where the enzyme is cellulase, pectinase, and the like, these enzymes catalyze the reaction in which cellulose, pectin, and the like included in the feedstuff or the like are degraded. Polysaccharides such as cellulose and pectin are a kind of the component constituting the cell walls of plants. Various kinds of the polysaccharides constituting the cell walls of plants have been known. The forms thereof are various and the constitutions are complex. In order to efficiently degrade the cell wall polysaccharide having complex structures, the degrading enzymes preferably act stepwise. For example, degradation efficiency of the cell walls of plant raw materials included in the feedstuff is improved by degrading cellulose, pectin, and the like with the enzymes such as cellulase and pectinase. Consequently, the feedstuff becomes easily digested.

For example, in the case where the enzyme is tannase, tannase catalyzes the chemical reaction in which tannin included in the feedstuff or the like is degraded. Some types of tannin form complexes by strongly bonding to polymers such as proteins. Tannin may exist in the state of being intricately entangled with the components constituting the cell walls of plants and may inhibit degradation of the cell walls. Degradation of tannin with tannase improves the degradation efficiency of the cell walls of plant raw materials included in the feedstuff and thus the feedstuff becomes easily digested.

For example, in the case where the enzyme is phytase, phytase catalyzes the chemical reaction in which inorganic form phosphoric acid is separated from phytic acid included in the feedstuff and the like. It is said that phytic acid inhibits absorption of minerals such as calcium and zinc included in the feedstuff into the body of an animal ingesting the feedstuff. Therefore, degradation of phytic acid with phytase improves the absorption ratio of minerals. Phosphorous generated by degradation of phytic acid is also absorbed into the body of the animals ingesting the feedstuff.

Examples of the enzyme include enzymes selected from the group consisting of amylase, alkaline protease, acidic protease, neutral protease, xylanase, β-glucanase, cellulase, tannase, phytase, lactase, lipase, pectinase such as polygalac-turonase, a xylanase-pectinase complex enzyme, and a cellulase-protease-pectinase complex enzyme. Any of these enzymes are enzymes coded from the genomic DNA of the filamentous fungi and expressed from the filamentous fungi of the wild strain. Gene manipulation may be performed so that two or more enzymes among these enzymes are highly expressed in the filamentous fungi.

Genetic transformation may be performed so that the above enzyme is highly expressed in the filamentous fungi as compared to the filamentous fungi of the wild strain not subjected to genetic transformation by using a known gene technological method. In the filamentous fungi, for example, it is known that the promoter of amylase (AmyB) or the promoter of enolase (enoA) has high expression amounts. A chimeric gene is obtained by bonding a gene that codes the target enzyme and a terminator sequence corresponding to the promotor by using a known method to these promoters for high expression. When this chimeric gene is introduced to the filamentous fungi by a known method, the filamentous fungi in which the target enzyme is highly expressed can be obtained. The analysis of the genome sequences of some filamentous fungi has already finished and the sequences are published in a database. The sequences of the gene that codes the high expression promoter, the terminator, and the target enzyme are searched by using such a database and the primer is designed. The designed primer and a template such as cDNA and genomic DNA are used to amplify the desired gene sequence with PCR. The amplified gene sequence is used when conducting the genetic transformation. At the time of the genetic transformation, the above chimeric gene may be introduced at the target position of the genome by using a known genome editing method or the above chimeric gene may be introduced at any position of the genome by introducing the chimeric gene into the cells of the filamentous fungi. In order to selectively culture the genetically transformed filamentous fungi, known marker genes such as niaD and ptrA may be used.

At the time of cloning the highly expressing gene, the genomic DNA or cDNA of the filamentous fungi of the same species as the genetically transformed filamentous fungi is preferably used as the template. When the gene incorporated into the genetically transformed filamentous fungi is derived from the filamentous fungi belonging to the same species, safety of filamentous fungi is secured because a foreign gene is not incorporated. Such a cloning method is referred to as self-cloning. The method of the self-cloning involves, for example, cloning the desired gene using the genomic DNA of the wild strain of the koji mold (*Aspergillus oryzae*, RIB40) obtainable at NBRC (National Institute of Technology and Evaluation) as the template, and subsequently introducing the cloned gene to a commercially available koji mold for sake brewing (*Aspergillus oryzae*, AOK11).

The solid-cultured product of the filamentous fungi is not particularly limited and can be obtained by, for example, the following method. The solid substrate described below is subjected to steaming and cooled. Seed fungi are inoculated to the cooled substrate. The inoculated substrate is placed on a culture bed in a culture apparatus and the culture is performed so that the filamentous fungi are propagated in the solid culture substrate by passing air in which temperature and humidity are controlled through between the grains of the culture substrate. The temperature of the air is not particularly limited. For example, the temperature is controlled in a range of 20° C. to 45° C. The humidity of the air is not particularly limited. For example, the humidity is controlled in a range of 50% to 99% in relative humidity. By such a method, the solid-cultured product in which the hyphae of the filamentous fungi are propagated on the surface and inside of the solid-like substrate can be obtained.

In the solid-cultured product in which the hyphae of the filamentous fungi are propagated on the surface and inside of the solid-like substrate, the filamentous fungi are vigorously propagated using the substrate as a nutrition source and thus a large amount of the enzymes having activity and a large amount of the polysaccharides constituting the hyphae are included. Therefore, according to the solid-cultured product, the decrease in productivity of livestock caused by stress can be remarkably reduced as compared to the case where the spores of the filamentous fungi are fed to livestock or the case where the spores of the filamentous fungi are mixed with the feedstuff for livestock and the mixed product is orally fed.

When the filamentous fungi are cultured in a state of solid, more kinds of enzymes are produced as compared to the case where the filamentous fungi are cultured in a state of liquid and the production amount of individual enzyme also becomes larger. Therefore, when the stress reliever produced by subjecting the filamentous fungi to a step of culturing the filamentous fungi in the state of solid is fed to livestock, the effect of reducing the decrease in productivity of livestock caused by stress becomes larger as compared to the case where the product made by culturing the filamentous fungi in the state of liquid is fed to livestock. From the above reason, the filamentous fungi are preferably subjected to the step of culturing the filamentous fungi in the state of solid at the time of the production of the stress reliever.

The above substrate may be, for example, a solid organic substance suitable for the filamentous fungi to breed. The solid includes, in addition to a solid content having hardness, a slurry-like substance or a power grain product. Examples of the substrate include one or more organic substances selected from the group consisting of cereals such as barleycorn, wheat, the bran of wheat, rice, beans, and corn; residues of processed food such as beet pulp, the squeezed lees of oil, and the squeezed lees of fermented foods; and food residues such as leftover foods. Examples of the squeezed lees of oil include the squeezed lees of soybean, the squeezed lees of rapeseed, the squeezed lees of sesame, and the squeezed lees of corn.

The dosage form of the stress reliever is not particularly limited. For example, the solid-cultured product obtained by solid-culturing the substrate with the filamentous fungi may be determined to be the stress reliever as it is, the solid-cultured product may be pulverized to form powder, or the solid-cultured product may be determined to be a liquid form or a slurry form by blending a liquid component to the solid-cultured product when the feedstuff fed to livestock is the liquid form or the slurry form. A feeding substances may be mixed with the solid-cultured product. Examples of the feeding substance include a bulk increasing material that enhances mixing ability with feedstuff, additives such as vitamin compounds, products generally fed such as known feedstuff for livestock, or a mixture of two or more of them. The solid-cultured product alone may be determined to be the stress reliever. In the case where the solid-cultured product alone is determined to be the stress reliever, for example, the feeding substance is not added to the solid-cultured product and the solid-cultured product is, for example, inspected and packaged to produce a finished product.

The blend ratio of the solid-cultured product and the feeding substance is not particularly limited. However, blend of an excessive amount of the solid-cultured product exhibits tendency in which the effect for relieving stress is saturated and thus increases the cost. Due to such tendency, the blend ratio (%) of the solid-cultured product is, for example, preferably 0.05% by mass to 5.0% by mass, more preferably 0.05% by mass to 4.0% by mass, and further preferably 0.05% by mass to 3.0% by mass. The effect for reducing the decrease in productivity of livestock at the time of stress load can be obtained even when the solid-cultured product is mixed with the feeding substance. The effect for relieving stress can be obtained even when the blend ratio of the solid-cultured product is, for example, 0.05% by mass, which is a small blend ratio.

Common feedstuffs of livestock are solid in many cases. In the case where the liquid cultured product of the filamentous fungi is mixed with the solid feedstuff, liquid part of the feedstuff is increased. This may cause deterioration in a taste property for livestock that is used to the solid feedstuff. In the case where the livestock is used to the solid feedstuff, the dosage form of the stress reliever is preferably solid. By doing this, deterioration in the taste property for the livestock can be prevented. When the solid-cultured product is determined to be the stress reliever as it is, processing is not necessary, which is more preferable.

Examples of relieved stress includes the followings: stress by breeding livestock in a dense state, stress by vaccination, stress by capturing livestock by hand, stress by restraining livestock, stress at the time of transporting livestock, stress in slaughterhouses, stress during an incubation period of eggs, stress at the time of cutting beaks or horns, stress by forced molting, stress by early weaning, stress by castration, stress by childbirth, stress by fasting, stress by feeding restriction, stress by placing livestock in a hot environment, stress by placing livestock in a cold environment, stress by noise, stress by light beams, or stress by weather.

The target livestock to which the stress reliever is fed is not particularly limited. Examples the livestock include chickens, cows, pigs, horses, donkeys, camels, goats, sheep, or fish such as carp and rainbow trout. The livestock include livestock of which meat is used, livestock of which eggs are used, and livestock of which milk, leathers, furs, hairs, or feathers are used.

The stress reliever has the effect for relieving stress of livestock and reducing the decrease in productivity. The decrease in productivity refers to the decrease in the production amount of products to be used such as meat, eggs, milk, hairs, and leathers obtained from livestock and deterioration in the quality of the products to be used. The decrease in the production amount includes a decrease in the ingestion amount of feedstuff. Examples of the decrease in productivity include body weight reduction, a decrease in the ingestion amount of feedstuff, a decrease in an egg weight, a decrease in an eggshell thickness, a decrease in a yolk weight, a decrease in a milking amount, hair loss, and deterioration in the quality of the products to be used.

EXAMPLES

Hereinafter, the method of producing the stress reliever and the stress reliever produced by the method will be described with reference to Examples. Examples to be described below are mere limited examples. The technical scope of the present invention is not limited to Examples.

Example 1

To the bran of wheat (wheat bran), water was added and the resultant mixture was stirred, and thereafter the bran of wheat was subjected to steaming treatment under a condition of 0.2 MPa. The steamed bran of wheat was cooled down to around 30° C. A certain amount of the seed fungi of *Aspergillus oryzae* (AOK11) that is commercially available as a koji mold for sake brewing and does not produce mold poison was inoculated and the resultant mixture was mixed so as to be uniform. The water content of the bran of wheat at the time of inoculation was set to 60%. The culture was started after this raw material was accumulated on the culture bed in the culture apparatus and smoothed so that the thickness of the accumulated raw material was constant. During the culture, air in which temperature and humidity were controlled was fed to the accumulated raw material and the fed air was passed through between the grains of the raw material. At this time, the temperature of the fed air was controlled to 25° C. to 40° C. and the relative humidity of the fed air was controlled to 90% to 96% so that the substance temperature of the raw material is in a range of 30° C. to 38° C. During the culture, the raw material was stirred using a stirring unit equipped with the culture apparatus. The culture was performed until hyphae of the filamentous fungi covered the surface of the grains of the bran of wheat. This solid-cultured product was determined to be the stress reliever according to Example 1 without sterilizing the fungi by heating or the like in a state where the solid-cultured product was alone as it was. This stress reliever includes the viable fungi of *Aspergillus oryzae* (AOK11) and includes useful enzymes of *Aspergillus oryzae* (AOK11) retaining enzyme activity.

Example 2

The cultured product of the solid bran of wheat was obtained in the same manner as the manner in Example 1 except that *Aspergillus oryzae* (AOK11) that highly expressed tannase (tan A), pectin lyase (pelA) that is a kind of pectinase, phytase (phyA), and polygalac-turonase (pgaB) that is a kind of pectinase was used as the seed fungi. This solid-cultured product was determined to be the stress reliever according to Example 2 without sterilizing the fungi by heating or the like in a state where the solid-cultured product was alone as it was. Similar to Example 1, this stress reliever includes the viable fungi and retains enzyme activity.

The target genes of tannase (tan A), pectin lyase (pelA), phytase (phyA), or polygalac-turonase (pgaB) were incorporated to *Aspergillus oryzae* (AOK11) by known methods to perform the genetic transformation. At the time of cloning the target genes, the genomic DNA of *Aspergillus oryzae* (RIB40) was used as the template. Each of the target genes described above was incorporated between the amylase promoter (AmyB promoter) sequence and the amylase terminator (AmyB terminator) sequence that are high expression promoters. The expression cassette that was a chimeric gene of thus prepared promotor sequence, the target gene sequence, and the terminator sequence was not incorporated to the plasmid but was introduced to *Aspergillus oryzae* (AOK11) by a chloroplast-PEG method. These gene sequences can be searched using a koji mold genome database (www.aspgd.org/) and the database of glycosyl hydrolase CAZy (www.cazy.org/fam/accGH.html).

Observation of Body Weight Change

A plurality of 14-day old hens for meat (Chunky) were bred by dividing into Experimental Section 1 to Experimental Section 3 described below to observe an effect in which hot environment stress affected the body weight change of the hens.

Experimental Section 1

As the feedstuff for the hens, from 14 days old to 20 days old, the stress reliever in Example 2 was mixed with the commercially available feedstuff for chick breeding (blended feedstuff for broiler fattening in former period Power Chicken, manufactured by NICHIWA SANGYO CO., LTD.) so that the stress reliever was contained in 2.0% by mass and the resultant mixture was fed to the hens. After 21 days old, the stress reliever in Example 2 was mixed with the feedstuff for latter period (Daisu-Meijin, manufactured by CHUBUSHIRYO CO., LTD.) so that the stress reliever was contained in 2.0% by mass and the resultant mixture was fed to the hens. On the day when the hens became 35 days old (the zeroth day described below), the hens were transferred to a poultry house having a hot environment to breed the hens. The hot environment refers to breeding in a poultry house having no windows where temperature control with an air conditioner is not performed. The temperature was in a range of 26° C. to 32° C. Experimental Section 1 included four hens.

Experimental Section 2

The hens were bred in the hot environment in the same manner as the manner in Experimental Section 1 except that the feedstuff was changed so that the stress reliever in Example 1 was contained in the same former period feedstuff or latter period feedstuff used in Experimental Section 1 in 2.0% by mass. Experimental Section 2 included six hens.

Experimental Section 3

The hens were bred in the hot environment in the mane manner as the Experimental Section 1 except that the feedstuff was changed so that the bran of wheat not subjected to the solid culture with the filamentous fungi was contained in the same former period feedstuff or latter period feedstuff used in Experimental Section 1 in 2.0% by mass. Experimental Section 3 included five hens.

Experimental Section 4

As the feedstuff for the hens, from 14 days old to 20 days old, the bran of wheat not subjected to the solid culture with the filamentous fungi was mixed with the commercially available feedstuff for chick breeding (blended feedstuff for broiler fattening in former period Power Chicken, manufactured by NICHIWA SANGYO CO., LTD.) so that the bran of wheat was contained in 2.0% by mass and the resultant mixture was fed to the hens. After 21 days old, the bran of wheat not subjected to the solid culture with the filamentous fungi was mixed with the feedstuff for latter period (Daisu-Meijin, manufactured by CHUBUSHIRYO CO., LTD.) so that the bran of wheat was contained in 2.0% by mass and the resultant mixture was fed to the hens. On the day when the hens became 35 days old (zeroth day), the hens were transferred to a poultry house having a thermal neutral zone to breed the hens. The thermal neutral zone refers to a temperature range suitable for homoiothermic animals. In this experiment, the air temperature was controlled to 22° C., which was suitable temperature to breed hens. Experimental Section 4 included six hens.

In Experimental Sections 1 to 4, the day when the hens were transferred to the hot environment or the thermal neutral zone to start breeding is determined to be the zeroth day. The next day is described as the first day, the day after the next day is described as the second day, and so forth.

The body weight (g) on the zeroth day was subtracted from the body weight (g) on the first day. The change in the body weights of the hens on the first day was recorded in each Experimental Section. The results are illustrated in the graph of FIG. 1. In the results of FIG. 1, the results obtained by averaging the body weights of the hens included in each Experimental Section are illustrated. Similarly, the results of FIGS. 2 to 6 described below are the averaged values.

From the zeroth day to the seventh day, the body weights of the hens were measured and recoded in each Experimental Section and the relation between the number of days after the hot environment treatment started and the body weight (g) of the hens was recorded. The results are illustrated in the graph of FIG. 2.

Figure 2:
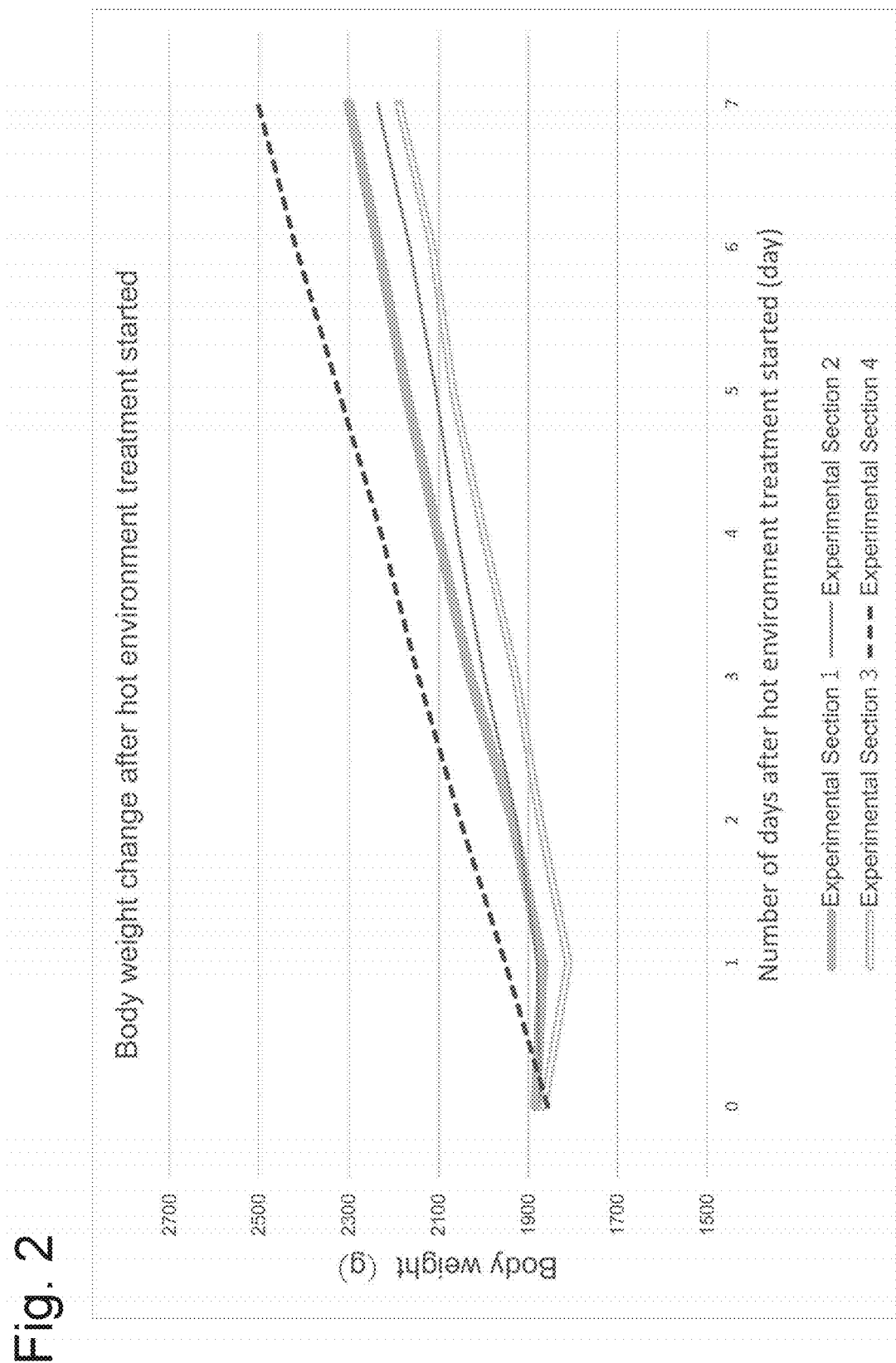
FIG. 2 is a graph illustrating the amount of body weight change (g) in a period from the day (the zeroth day) when the hot environment treatment started to the seventh day.

As is obvious from the graphs of FIG. 1 and FIG. 2, it is found that the hens in Experimental Section 1 to which the stress reliever in Example 2 was fed or the hens in Experimental Section 2 to which the stress reliever in Example 1 was fed reduce the decrease in the body weight caused by hot environment stress in the initial stage where the hot environment stress was applied as compared with the hens in Experimental Section 3 to which the bran of wheat not inoculated with the filamentous fungi was fed. As illustrated in the graph of FIG. 2, the hens in Experimental Section 1 to which the stress reliever in Example 2 containing *Aspergillus oryzae* that highly expressed various enzymes was fed indicate a larger slope of the graph in the latter period of the experiment and thus have an earlier increase in the body weight as compared with the hens in Experimental Section 2 to which the stress reliever in Example 1 containing *Aspergillus oryzae* of the wild strain was fed.

Observation of Change in Production Amount of Eggs

A plurality of 259-day old hens (White Leghorn) for egg production were bred by dividing the hens from Experimental Section 5 to Experimental Section 7 to observe the effect in which the hot environment stress affected change in the feedstuff ingestion amount.

Experimental Section 5

The feedstuff for the hens and the stress reliever in Example 2 were mixed so that the stress reliever in Example 2 was contained in the feedstuff for the hens in 2.0% by mass and the resultant mixture was fed to the hens. As a feedstuff for the hens, the commercially available blended feedstuff for adult chickens (High Egg, manufactured by Marubeni Nisshin Feed Co., Ltd.) was used. The day when the feedstuff was changed is determined to be the zeroth day. The hens were bred in a poultry house where the temperature was controlled to 25° C. with an air conditioner from the zeroth day to the morning of the fourth day and bred in a poultry house having no windows under the hot environment (28° C. to 36° C.) from the afternoon of the fourth day. Experimental Section 5 included seven hens.

Experimental Section 6

The feedstuff (High Egg, manufactured by Marubeni Nisshin Feed Co., Ltd.) alone not including the solid-cultured product of the filamentous fungi was fed to the hens. The hens were bred in a poultry house where the temperature was controlled to 25° C. with an air conditioner from the zeroth day to the morning of the fourth day and bred in the poultry house having the same hot environment as the environment in Experimental Section 5 from the afternoon of the fourth day. Experimental Section 6 included five hens.

Experimental Section 7

Feedstuff (High Egg, manufactured by Marubeni Nisshin Feed Co., Ltd.) alone not including the solid-cultured product of the filamentous fungi was fed to hens. The hens were bred in a poultry house where the temperature was controlled to 25° C. with an air conditioner from the zeroth day to the morning of the fourth day and bred in the poultry house having the same thermal neutral zone as the above said Experimental Section 4 from the afternoon of the fourth day. Experimental Section 7 included six hens.

Figure 3:
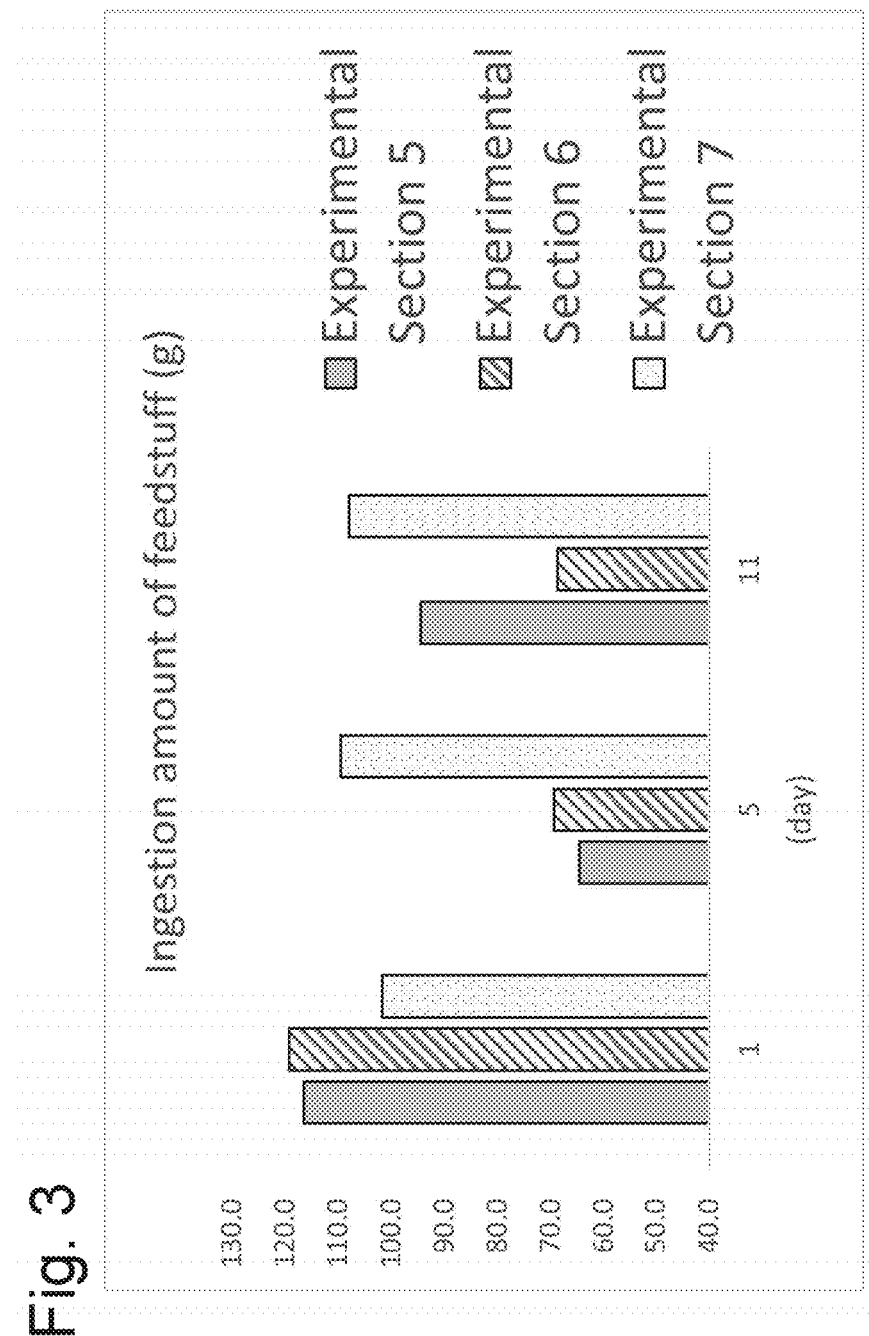
FIG. 3 is a graph illustrating a relation between the number of days after the hot environment treatment started and the ingestion amount (g) of feedstuff.

On the first day, the fifth day, and the eleventh day, the ingestion amounts of the feedstuff in each Experimental Section were recorded. The relation between the number of days after the hot environment treatment started and the ingestion amount (g) of the feedstuff is illustrated in the graph of FIG. 3. The time of the ingestion of the feedstuff is limited from 15 o'clock on the day to 15 o'clock on the next day. The ingestion amount of the feedstuff was determined by weighing the feed tank before feeding and after feedstuff ingestion and calculating the difference.

As is obvious from the graph of FIG. 3, it is found that the hens in Experimental Section 5 to which the stress reliever in Example 2 was fed had a larger ingestion amount of the feedstuff on the eleventh day as compared to the hens of Experimental Section 6 to which the feedstuff alone was fed. It is found that the stress reliever in Example 2 has the effects of reducing stress, promoting recovery of the feedstuff ingestion amount, and reducing the decrease in productivity when the hot environment stress is applied.

Inspection of Egg Quality and the Like

Eggs that the hens in each Experimental Section laid were collected and the quality and the like of the eggs on the fourth day and the eleventh day were inspected. The inspection items were an egg weight, an eggshell weight, and a yolk weight. The egg weight refers to an entire weight (g) of one egg containing eggshell, egg white, and yolk. The eggshell weight refers to the weight (g) of the eggshell per egg. The yolk weight refers to the weight (g) of yolk alone separated from the egg. The relation of the number of days after the hot environment treatment started and the egg weight, eggshell weight, or yolk weight is illustrated in the graphs of FIG. 4 to FIG. 6.

Figure 4:
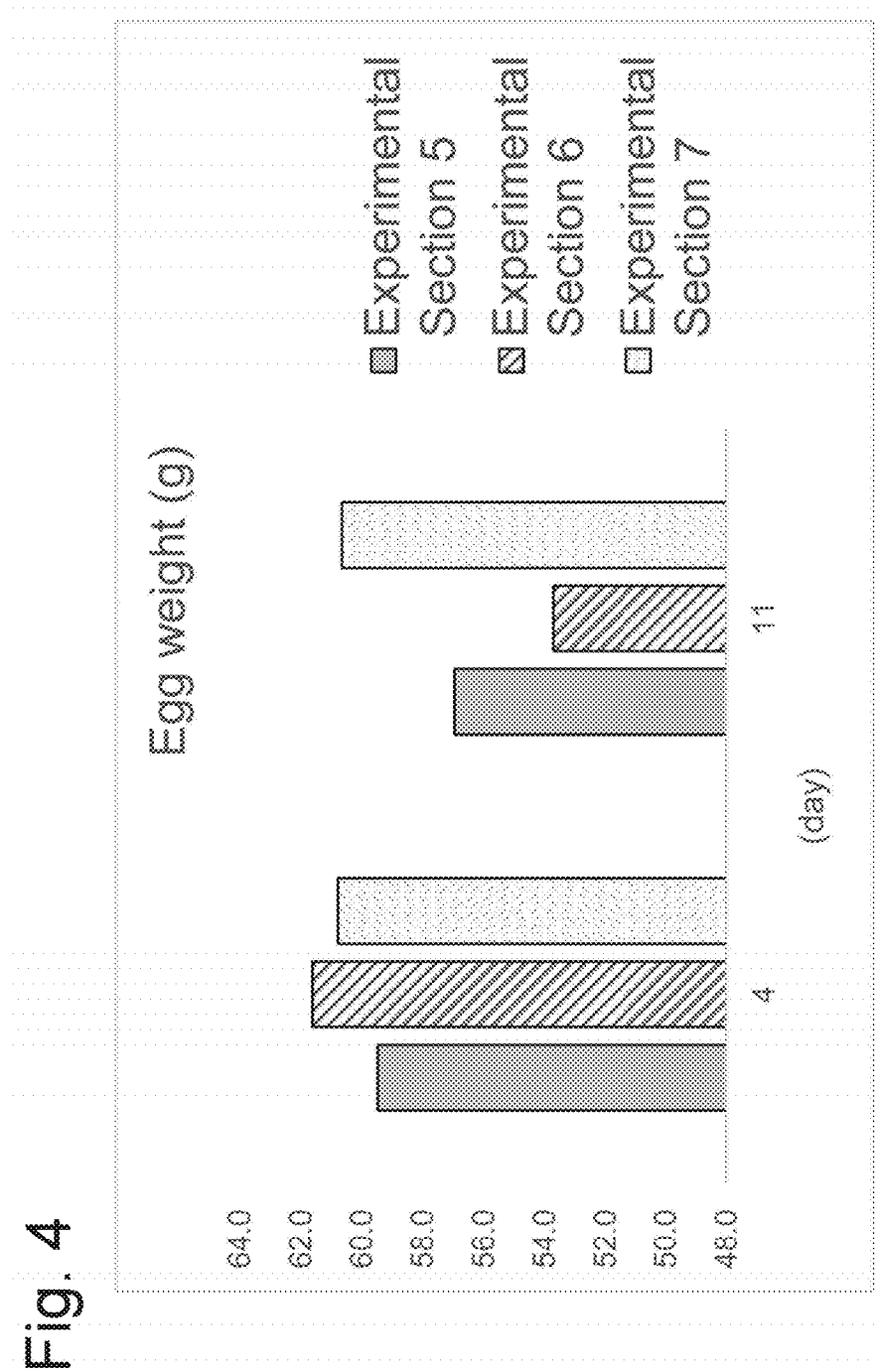
FIG. 4 is a graph illustrating a relation between the number of days after the hot environment treatment started and an egg weight (g).
Figure 5:
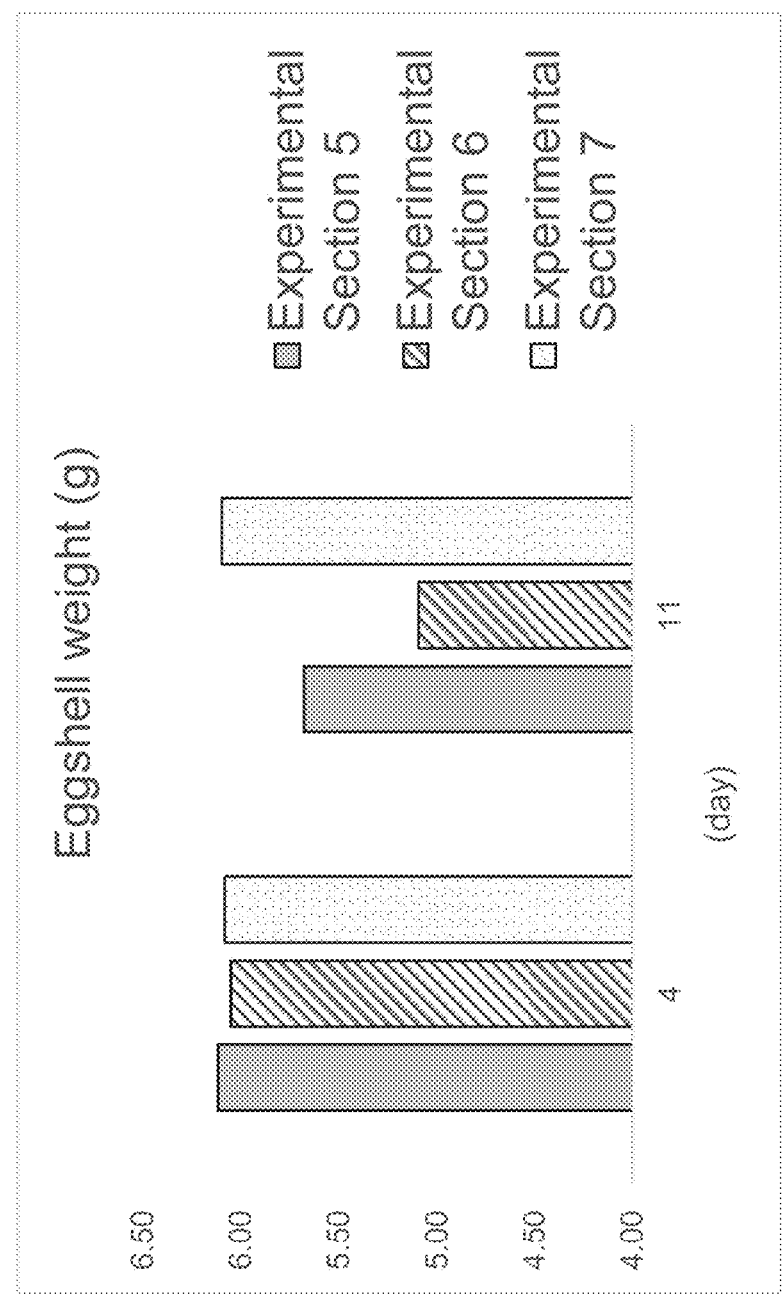
FIG. 5 is a graph illustrating a relation between the number of days after the hot environment treatment started and an eggshell weight (g).
Figure 6:
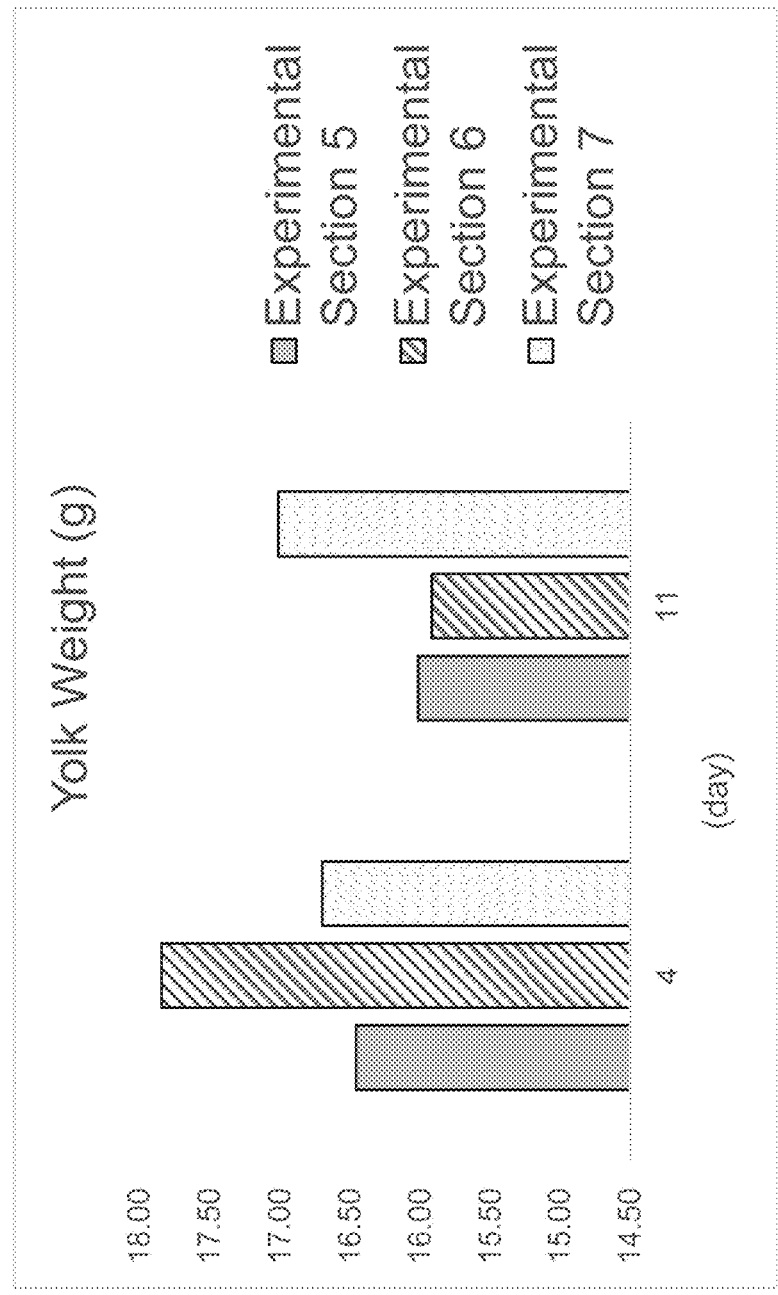
FIG. 6 is a graph illustrating a relation between the number of days after the hot environment treatment started and a yolk weight (g).

As is obvious from the graphs of FIG. 4 to FIG. 6, it is found that a decrease in each of the egg weight, the eggshell weight, and the yolk weight of the hens in Experimental Section 5 to which the stress reliever in Example 2 was fed is reduced on the eleventh day as compared to that of the hens in Experimental Section 6 to which the feedstuff alone was fed. It is found that the stress reliever in Example 2 has the effects of reducing the decrease in the egg quality such as the egg weight, the eggshell weight, that is, the eggshell thickness, and yolk weight for a long period when the hot environment stress is applied.

As described above, feeding of the stress reliever to livestock allows the decrease in productivity such as the decrease in the production amount of eggs or the deterioration in quality of eggs when the stress is applied to be reduced in the case where the livestock is livestock laying eggs when the stress is applied to the livestock. For example, feeding of the stress reliever to livestock allows the decrease in productivity such as the decrease in the production amount of meat or the deterioration in quality of meat when the stress is applied to be reduced in the case where the livestock is livestock that does not lay eggs. For the stress reliever, the effect of reducing a decrease in the production mount of leathers, hairs, or milk or deterioration in the quality of these products was also observed.

The invention claimed is:

1. A method for relieving stress of livestock, the method comprising:
   accumulating a substrate inoculated with filamentous fungi on a culture bed;
   stirring the substrate using a stirring unit equipped with a culture apparatus while supplying air so that the air passes through between grains of the substrate attached with the filamentous fungi;
   feeding the solid cultured product to livestock; and
   reducing a decrease in productivity of livestock at the time of exposing livestock to a hot environment stress, wherein
   the filamentous fungi is *Aspergillus oryzae* that does not produce mold poison,
   the filamentous fungi is a transformant that is genetically manipulated so that enzymes selected from the group consisting of amylase, alkaline protease, acidic protease, neutral protease, xylanase, β-glucanase, cellulase, tannase, phytase, lactase, lipase, pectinase, a xylanase-pectinase complex enzyme, and a cellulase-protease-pectinase complex enzyme are expressed, and said enzymes are highly expressed in the filamentous fungi as compared to filamentous fungi of a wild strain.

2. The method for relieving stress of livestock according to claim 1, wherein feeding the solid cultured product reduces one or more decreases in productivity of livestock at the time of stress load by relieving stress of livestock ingesting the solid cultured product, the one or more decreases being among body weight reduction, a decrease in an ingestion amount of feedstuff, a decrease in an egg weight, a decrease in an eggshell thickness, and a decrease in a yolk weight.

3. The method for relieving stress of livestock according to claim 1, wherein the solid-cultured product comprises polysaccharides constituting hyphae of the filamentous fungi.

4. The method for relieving stress of livestock according to claim 1, wherein the solid-cultured product comprises an enzyme having activity.

5. The method for relieving stress of livestock according to claim 1, wherein the solid-cultured product comprises viable fungi of the filamentous fungi.

6. The method for relieving stress of livestock according to claim 1, the solid-cultured product that is fed to livestock is blended with a feeding substance.

7. The method for relieving stress of livestock according to claim 6, a blend ratio of the solid-cultured product to the feeding substance is 0.05% by mass to 5.0% by mass.

8. The method for relieving stress of livestock according to claim 1, the solid-cultured product alone is fed to livestock.

* * * * *